United States Patent [19]

Cole et al.

[11] Patent Number: 4,487,761
[45] Date of Patent: Dec. 11, 1984

[54] DOPAMINE β-HYDROXYLASE INHIBITORS

[75] Inventors: Lucille J. Cole, Roselle Park; Leeyan Huang, Westfield; Jerrold M. Liesch, Princeton Junction, all of N.J.

[73] Assignee: Merck & Co., Inc., Rahway, N.J.

[21] Appl. No.: 365,741

[22] Filed: Apr. 5, 1982

[51] Int. Cl.³ .................. A61K 35/00; A61K 31/44; C12P 1/04; C07D 403/00
[52] U.S. Cl. .................. 424/118; 424/263; 435/170; 546/296
[58] Field of Search ............ 424/118, 263; 435/170; 546/296

[56] References Cited

U.S. PATENT DOCUMENTS 3,914,239  10/1975  Kuhnis et al. .............. 260/295 R
3,998,955  12/1976  Kuhnis et al. .............. 424/266
4,009,077   2/1977  Tanabe et al. .............. 195/81

FOREIGN PATENT DOCUMENTS 1246727  9/1971  United Kingdom .

Primary Examiner—Jerome D. Goldberg
Attorney, Agent, or Firm—William H. Nicholson

[57] ABSTRACT

Two fermentation isolates, $C_7H_9NO_4$ and $C_6H_7NO_3$, presumably trihydroxy, methyl-pyridine derivatives, are inhibitors of dopamine β-hydroxylase. These natural product compounds are produced by fermentation of *Streptoverticillium hiroshimense* and each may prove useful as antihypertensive agents.

6 Claims, No Drawings

DOPAMINE β-HYDROXYLASE INHIBITORS

BACKGROUND OF THE INVENTION

A number of substituted pyridine compounds, both natural products and synthetic compounds, have been shown to exhibit dopamine β-hydroxylase inhibitory action and have been employed as antihypertensive agents. See for example; Tanabe et al., U.S. Pat. No. 4,009,077 on phenopicolinic acid natural products, Umezawa et al., Great Britian Patent Specification No. 1,246,727 on fusaric acid natural products and Kuhnis et al., U.S. Pat. Nos. 3,914,239 and 3,998,955 on synthetic substituted pyridine-2-carboxylates.

SUMMARY OF THE INVENTION

The instant invention is directed to the individual dopamine β-hydroxylase inhibitors produced by the controlled aerobic fermentation of *Streptoverticillium hiroshimense*, ATCC No. 39070 in an aqueous nutrient medium, and a process for their isolation.

DETAILED DESCRIPTION OF THE INVENTION

The present invention is directed to the two individual natural product dopamine β-hydroxylase inhibitors, and their isolation from the fermentation broth of *Streptoverticillium hiroshimense*, ATCC No. 39070. These two compounds, having empirical formulae $C_7H_9NO_4$ and $C_6H_7NO_3$, are best represented by the generic structures I and II:

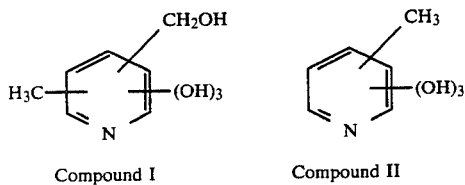

Compound I     Compound II where the exact position of the substituent groups is not well defined.

The present invention is also directed to a method of producing the dopamine β-hydroxylase inhibitors Compounds I and II, characterized by fermenting a dopamine β-hydroxylase inhibitor producing strain of *Streptoverticillium hiroshimense*, ATCC No. 39070 in an aqueous nutrient medium under controlled aerobic conditions and isolating the accumulated Compounds I and II from the cultured broth.

*Streptoverticillium hiroshimense*, ATCC No. 39070 represents a new strain of a known microorganism. A biologically pure sample of this living organism has been deposited without restriction in, and made a part of, the American Type Culture Collection, Rockville, Md., from which it is available under Accession No. ATCC 39070.

MORPHOLOGICAL AND CULTURAL CHARACTERISTICS OF STREPTOVERTICILLIUM HIROSHIMENSE ATCC NO. 39070

The cultural and morphological characteristics described herein have been compared to those descriptions of Streptoverticillium in Bergey's *Manual of Determinative Bacteriology*, 8th Edition, The Williams and Wilkins Company. The data shown below confirms the designation of the culture ATCC No. 39070 as *Streptomyces hiroshimense*. Differences are minor and of a strain differentiating nature.

The cultural characteristics of *Streptoverticillium hiroshimense* ATCC No. 39070 are as follows: (V=vegetative growth; A=aerial mycelium; SP=soluble pigment)

Morphology: Sporophores form short branches produced in a verticil or whorl at intervals along the aerial mycelia. These branches in turn produce several secondary branches that form straight chains of approximately 10 spores.

Oatmeal agar (ISP Medium 3)
  V: Reverse—dark rose-red
  A: Flat, velvety, rose-beige (4ec)
  SP: None
Czapek Dox agar (sucrose nitrate agar)
  V: Very poor growth—whitish
  A: Scant—whitish
  SP: None
Egg albumin agar
  V: Reverse—Bright pink
  A: Flat, velvety, rose-beige (4ec) edged with vectors of deeper rose-beige and shell pink (4ca)
  SP: None
Glycerol asparagine agar (ISP Medium 5)
  V: Reverse—deep orangish-red
  A: Flat, velvety, rose-beige (4ec)
  SP: None
Inorganic salts-starch agar (ISP Medium 4)
  V: Reverse—deep rose-pink
  A: Rose-beige (4ec) with flecks of bright pink
  SP: None
Yeast extract-malt extract agar (ISP Medium 2)
  V: Reverse—bright orangish-red
  A: Rose-beige (4ec), velvety
  SP: None
Peptone-iron-yeast extract agar
  V: Tan
  A: None
  SP: Light brown
  Melanin: None
Nutrient tyrosine agar
  V: Reverse—dark brown with some red in it
  A: Sparse—reddish gray
  SP: Dark brown
  Decomposition of tyrosine: Tyrosine crystals decomposed
Tyrosine Agar (ISP Medium 7)
  V: Reverse—dark reddish-brown edged with red
  A: Beige edged with rose-beige
  SP: Light yellowish-reddish-brown
Carbon utilization
  Pridham-Gottlieb basal medium+1% carbon source;
  + =growth; ± =growth poor or questionable;
  − =no growth as compared to negative control (no carbon source)
  Glucose: + +
  Arabinose: −
  Cellulose: −
  Fructose: +
  Inositol: + +
  Lactose: ±
  Maltose: + +
  Mannitol: −
  Mannose: + +
  Raffinose: −
  Rhamnose: −

Sucrose: ±
Xylose: +
Temperature range (Yeast extract-dextrose+salts agar)
   28° C.—Good vegetative and aerial growth and sporulation
   37° C.—Good vegetative and aerial growth and sporulation
   50° C.—No growth
Oxygen requirement (Stab culture in yeast extract-dextrose+salts agar) Aerobic All readings taken after three weeks at 28° C. unless noted otherwise. pH of all media approximately neutral (6.8–7.2).

Color number designations taken from Color Harmony Manual, 1958, 4th Edition, Container Corporation of America, Chicago, Ill.

It is to be understood that for the production of the dopamine β-hydroxylase inhibitors, Compounds I and/or II, the present invention is not limited to the use of *Streptoverticillium hiroshimense* ATCC 39070. It is especially desired and intended that there be included the use of natural or artificial mutants produced from the described organism, or other variants of the genus Streptoverticillium, as far as they can produce the dopamine β-hydroxylase inhibitors, Compound I and/or Compound II. The artificial production of mutant Streptoverticillium from ATCC 39070 may be achieved by a conventional operation such as X-ray or ultraviolet (UV) irradiation of *Streptoverticillium hiroshimense* ATCC 39070, or by the use of chemical mutagens such as: nitrogen mustards, nitrosoguanidine and the like.

In the instant invention the dopamine β-hydroxylase inhibitor Compounds I and II are produced by the cultivation of the microorganism, *Streptoverticillium hiroshimense* ATCC 39070 at a temperature range from about 26° C. to 30° C. preferably 28° under aerobic conditions. Generally, the composition of the nutrient medium may be varied over a wide range. The essential nutrient ingredients are; a carbon source, and a nitrogen source. Other essential nutrients are provided via the mineral salts such as the chlorides, nitrates, sulfates, carbonates, and phosphates of sodium, potassium, ammonium and calcium. The nutrient medium may also contain sources of inorganic trace elements such as magnesium, iron, copper, manganese, zinc, cobalt and the like.

Cultivation is most productive in the pH range of from about 6.0 to 8.0.

Typical sources of carbon include: glucose, maltose, sucrose, dextrin, oils, starches, glycerol, and the like. Typical nitrogen sources include vegetable meals and extracts (e.g., malts, soy, cotton seed, figs, tomato, corn, etc.), animal viscera, various hydrolysates (casein, yeast, etc.), and fermentation by-products such as whole yeast and distillers solubles.

The maximum yield of dopamine β-hydroxylase inhibitor Compounds I and II can be achieved within about 70 to 120 hours, usually in about 96 hours of fermentation under optimum conditions. The inoculum for the fermentation may be provided from vegetative growth in a medium which supports rapid growth of the organism such as those set out below in Table IV.

Following cultivation, the dopamine β-hydroxylase inhibitor Compounds I and II may be recovered from the cultured broth by conventional chromatographic means. Generally, the whole broth is filtered through a filter aid to remove suspended solids, the filtrate is adjusted in pH, and ion-exchange chromatography is used to afford the purified products.

CHARACTERIZATION OF THE DOPAMINE β-HYDROXYLASE INHIBITORS COMPOUNDS I and II

Changes in the ultraviolet spectra of Compounds I and II in acid and base (see Table I) are comparable to the spectra of pyridoxin (vitamin $B_6$) and related compounds. Combining this UV data with the mass spectral (Table II) and proton NMR data (see Table III) the following generic structures are suggested for Compounds I and II:

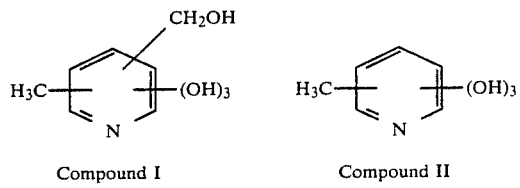

Compound I     Compound II

TABLE I

Ultraviolet (UV) Data γ
Acidic - Basic Aqueous Solutions
Compounds I and II

| Compound I | | Compound II | |
|---|---|---|---|
| Acidic | Basic | Acidic | Basic |
| 276 nm | 304 nm | 272 nm | 308 nm |
| 261 sh | 227 sh | 259 sh | 226 sh |

γnm - nanometers - $\lambda_{max}^{H_2O}$ at 25° C.
γsh - shoulder - also in nanometers

TABLE II

Mass Spectral Data - Compounds I and II m/e (abundance)

| Compound I | | |
|---|---|---|
| M+ | 171.0525 | (100%; calcd $C_7H_9NO_4$, 171.0532) |
| | 153.0449 | (54%; calcd $C_7H_7NO_3$, 153.0426) |
| | 125.0589 | (32%; calcd $C_7H_9O_2$, 125.0603) |
| | 112.0398 | (74%; calcd $C_5H_6NO_2$, 112.0399) |
| Compound II | | |
| M+ | 141.0399 | (100%; calcd $C_6H_7NO_3$, 141.0426) |
| | 112.0396 | (39%; calcd $C_5H_6NO_2$, 112.0399) |

TABLE III

Proton NMR Data γ
Acidic - Basic $D_2O$ solutions
Compounds I and II

| Compound I | | Compound II | |
|---|---|---|---|
| Acidic | Basic | Acidic | Basic |
| 2.48 | 2.30 | 2.48 | 2.29 |
| 4.82 | 4.68 | — | — |
| — | — | 7.74 | 7.09 |

γData is chemical shift (δ) in ppm downfield from an internal standard set at δ = 0.00.

Referring in detail to Table III, the chemical shift of the methyl group (2.48 in H+) in both Compounds I and II suggests the ortho substitution position and the similar upfield acid to base shifts for the $CH_3$ and $CH_2OH$ protons in Compound I suggests either the ortho or the para position for the $CH_2OH$ group. By comparison with the pyridoxins and on biogenetic grounds, the latter assignment is favored. Moreover, if Compound II is derived biogenetically from Compound I through loss of the $CH_2OH$ group, the chemical shift of the aromatic proton as well as its acid to base upfield shift is consistent with the para position on the basis of simple model compound comparison. Therefore the structures A and B are suggested for Compounds I and II, respectively:

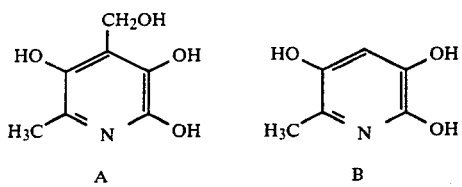

DOPAMINE β-HYDROXYLASE INHIBITION

(A) Dopamine β-Hydroxylase

Dopamine β-hydroxylase was obtained from beef adrenal glands. Minced adrenals were homogenized with 0.025M potassium phosphate buffer (pH—6.4) and centrifuged. The supernatant was adjusted to a final concentration of 1% Triton X-100 (Calbiochem. Inc.) by the addition of one-fourth volume of a 5% Triton X-100 solution and stirred at room temperature for 30 minutes. The Triton X-100 treated supernatant was centrifuged, and fractionated with a 66% aqueous ammonium sulfate solution. The resulting precipitate was homogenized in 0.025M potassium phosphate buffer (pH=6.4) and dialyzed. The dialysate was applied to a DE-52 Cellulose Column (Whatman Co.), pre-equilibrated with 0.005M potassium phosphate buffer (pH=6.4), and preloaded with about 2 cm of acid-washed activated carbon, located directly above the cellulose resin. The column was washed with 0.005M potassium phosphate buffer (pH=6.4) and eluted wih a linear gradient of 0.005M potassium phosphate buffer (pH=6.4) and 0.02M potassium phosphate buffer containing 0.1M potassium chloride. The active fractions were pooled and concentrated in small dialysis tubing under reduced pressure. The concentrated enzyme solution contains about 272 mg of protein with a specific activity of 1077 (starting material—about 17.8 g of protein). The concentrated enzyme solution was diluted with bovine serum albumin solution (0.2 mg/ml in 0.065M acetate buffer, pH=5.5) before being used in the enzyme inhibition assay.

(B) Dopamine β-Hydroxylase Inhibition Assay

The assay for the dopamine β-hydroxylase inhibition was carried out in a 1 ml incubation mixture containing 5 mM tyramine (freshly prepared), 1.5 mM ascorbic acid (prepared monthly), 0.4 mM sodium fumarate, 0.045 mM pargyline, catalase (25 mg per ml, 500 units) and 0.065M sodium acetate buffer, pH 5.5. The inhibitor, Compound I or II (see preparation and isolation below) was dissolved in 50% (v/v) aqueous methanol and 25 μl of this solution was added to the assay mixture. An enzyme reaction control was run by adding 25 μl of 50% (v/v) aqueous methanol to the assay mixture. The reaction was initiated by the addition of enzyme (4 μg of enzyme and 10 μg of bovine serum albumin) and the reaction mixture was incubated at 37° C. for 10 minutes. The reaction was terminated by adding 0.3 ml of a mixture of 3N NH4OH and 2% sodium periodate (2:1 ratio). Immediately, the solution was mixed and placed in an ice bath. After incubation in the ice bath for 10 min., the reaction mixture was acidified with 0.7 ml of 2.5N HCl containing $5 \times 10^{-4}$M EDTA and extracted with 2 ml of ethyl acetate pre-saturated with water. The assay mixtures were then centrifuged at 1500×g for 3 minutes. The optical absorbance of the organic phase was measured at 280 nm. A blank was run under the same conditions with the exception that the enzyme was added after the solution was placed in the ice bath for several minutes.

As determined in the assay described above, the $I_{50}$ (inhibition median) for Compound I was about 27 ng/ml and the $I_{50}$ for Compound II was about 37 ng/ml.

From the foregoing data it is expected that the dopamine β-hydroxylase inhibitor Compounds I and II will show antihypertensive activity in humans. From this data, an effective daily dosage range of about 50 mg/kg to 250 mg/kg would be expected to demonstrate this activity. Compounds I or II may be conveniently administered in unit dosage forms in single or multiple divided doses.

The dopamine β-hydroxylase inhibitors, Compounds I and II or a mixture thereof may be combined with appropriate pharmaceutical carriers in any manner known in the art of compounding. For example, suitable routes of administration may include oral, parenteral, intramuscular, and the like. The appropriate dosage forms are exemplified by tablets, troches, dispersions, suspensions, solutions, capsules and the like for oral administration; suspensions, solutions, emulsions and the like for administration by injection.

Typical pharmaceutical dosage forms that may be useful for the administration of the compounds of the present invention are given in the following examples.

EXAMPLE I

| Capsule Ingredients | Amount |
| --- | --- |
| Dopamine β-hydroxylase inhibiting Compound I or II | 100 mg |
| Lactose | 100 mg |
| The ingredients are mixed and filled into a hard gelatin capsule. | |
| Dopamine β-hydroxylase inhibiting Compound I or II | 100 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE II

For 100 tablets containing 100 mg of either of the dopamine β-hydroxylase inhibitors, Compounds I and II:

| Tablet Ingredients | Amount |
| --- | --- |
| Dopamine β-hydroxylase inhibiting Compound I or II | 10 g |
| Anhydrous Lactose USP | 21.7 g |
| Starch (directly compressible) | 3 g |
| Magnesium Stearate | 0.3 g |

The components are sieved through a 250 μm sieve and intimately mixed in a blender. The blended solids are compressed between 8.5 mm diameter punches in a tableting machine.

EXAMPLE III

| Oral Syrup Ingredients | Amounts |
| --- | --- |
| Dopamine γ-hydroxylase inhibiting Compound I or II | 1.0% w/v |
| Sorbitol Solution | 60.0% v/v |
| Dilute Hydrochloric Acid | as required |
| Flavoring | as required |
| Distilled Water | q.s. to 100% |

Compounds I or II are dissolved in water and the pH is adjusted as necessary with the dilute hydrochloric acid. The sorbitol solution, flavoring and remaining water are added and the pH is again adjusted if necessary. The syrup is clarified by filtration through suitable cellulosic filter pads.

The following examples illustrate the preparation and isolation of Compounds I and II from the fermentation of *Streptoverticillium hiroshimense*, ATCC 39070.

For Examples IV–VI, Table IV describes the various nutrient media used. For convenience, references in the examples to the various seed and production media will be identical to the indicia used in Table IV.

The terms "seed" and "production" media are employed as terms of art. Generally, a seed medium exhibits rapid growth of the desired microorganism and an aliquot of this medium is employed as a "seed" when another medium is used for the high yield production of the microorganism. Generally, a production medium produces a higher yield of the desired compounds.

TABLE IV
NUTRIENT MEDIA COMPOSITION

| (1) Medium (1) | |
| --- | --- |
| Dextrose | 1.0 g |
| Starch, Soluble | 10.0 g |
| Beef Extract | 3.0 g |
| Yeast Autolysate (Ardamine) | 5.0 g |
| NZ Amine Type E | 5.0 g |
| $MgSO_4.7H_2O$ | 0.05 g |
| Phosphate Buffer | 2.0 ml |
| $CaCO_3$ | 0.5 g |
| Distilled Water | 1000 ml |
| pH = 7.0–7.2 (adjust with NaOH) | |
| (2) Medium (2) | |
| Tomato Paste | 20.0 g |
| Primary Yeast | 10.0 g |
| Dextrin (Amidex) | 20.0 g |
| $CoCl_2.6H_2O$ | 5.0 mg |
| Distilled Water | 1000 ml |
| pH: adjust to 7.2–7.4 using NaOH | |
| (3) Medium (3) | |
| Glycerol | 4.0 ml |
| Dextrose | 2.0 g |
| Malt Extract | 6.0 g |
| Corn Steep Liquor | 16.0 ml |
| Pharmamedia | 4.0 g |
| Cod Liver Oil | 1.0 g |
| Ardamine | 0.4 g |
| Humic Acid | 0.08 g |
| pH 7.0 | |
| Distilled Water | 1000 ml |

EXAMPLE IV

A Medium 1 slant (see Table IV) of *Streptoverticillium hiroshimense*, ATCC 39070 was used to inoculate, using aseptic techniques, a seed flask containing 54 ml of Medium 1. The seed flask was shaken at 28° C. on a 220 rpm shaker (2" throw) for 3 days after which time good growth was obtained. The broth from this flask was used to inoculate a production flask containing 40 ml of production Medium 2 (see Table IV). The inoculum was about 7 ml of the seed broth. The production flask was shaken at 220 rpm at 28° C. for 4 days, at which time the broth was harvested.

EXAMPLE V

A lyophilized Medium 1 sample of *Streptoverticllium hiroshimense*, ATCC 39070 was used to inoculate, using aspectic techniques, a seed medium 250 ml baffled Erlenmeyer flask containing 54 ml of Medium 1 (see Table IV). After 1 day of incubation at 28° C. with agitation at 220 rpm (2" throw), a portion of this broth (2 ml) was used to inoculate a 250 ml unbaffled Erlenmeyer production flask containing 40 ml of production Medium 3 (see Table IV). After 4 days incubation at 28° C. with agitation 220 rpm (2" throw), the broth was harvested.

EXAMPLE VI

A lyophilized Medium 1 sample of *Streptoverticillium hiroshimense*, ATCC 39070 was used to inoculate 54 ml of seed Medium 1 (see Table IV). This flask was agitated at 220 rpm (2" throw) at a temperature of 28° C. for 1 day. A 10 ml portion of this broth was used to inoculate, using aseptic techniques, 500 ml of seed Medium 1 in a baffled two liter Erlenmeyer flask. After incubation at 28° C. with 220 rpm agitation, the entire contents of this flask were used to inoculate 9.5 liters of production Medium 2 (see Table IV). The fermentor was operated for 71 hours at 28° C. with 400 rpm agitation and an air flow of 3 liters per minute after which time the broth was harvested.

ISOLATION OF COMPOUNDS I AND II

After cultivation of *Streptoverticillium hiroshimense*, ATCC 39070, the dopamine β-hydroxylase inhibiting Compounds I and II can be recovered from the harvested broth by conventional chromatographic means.

EXAMPLE VII

The general scheme of purification involves passage of the combined harvested broths from examples IV–VI through a filter aid such as a Celite pad. The filtrate is then adjusted to about pH 9 with an aqueous base such as 2.5N ammonium hydroxide. The basic filtrate is then passed through a 1.6 liter Dowex 1×2 mesh ($OH^-$ cycle) resin column. The effluent from this basic ion-exchange column is adjusted to about pH 3 with an aqueous acid such as 2.5N hydrochloric acid and adsorbed onto a 900 ml Dowex 50×2 mesh ($H^+$ cycle) resin column. This acidic ion-exchange column is then washed with water, and the active component is eluted using 1 liter of 1N $NH_4OH$. The eluate was concentrated to about half its volume (about 500 ml) and lyophylized. The resulting solid material was extracted with methanol and the undissolved residue was dissolved into water. One half of this aqueous solution was chromatographed on a 200 ml Bio-Rad P-2 (polyacrylamide gel permeation) column using water as the eluting system. Active fractions were combined and rechromatographed on a 175 ml Pharmacia G-10 (dextran gel permeation) column using water. Two fractions, representing Compounds I and II were obtained from this second column. One fraction contained only Compound II (1.89 mg) while the second fraction was comprised of a mixture of Compounds I and II. Upon cooling to 0° C., Compound I crystallized from this second fraction, affording 2.36 mg of Compound I as colorless crystals.

What is claimed is:

1. A dopamine β-hydroxylase inhibitor of structural formula I:

H₃C—[pyridine ring with CH₂OH and (OH)₃ substituents]—N empirical formula $C_7H_9NO_4$, and physical chemical characteristics:
 a. colorless crystalline compound,
 b. acidic aqueous UV data: 276 nm   261 sh,
 c. basic aqueous UV data: 304 nm   227 sh,
 d. acidic NMR (D₂O) chemical shifts: 2.48 (s)   4.82 (s),
 e. basic NMR (D₂O) chemical shifts: 2.30 (s)   4.68 (s),
 f. mass spectral data:
   M+ 171.0525 (100%)
   153.0449 (54%)
   125.0589 (32%)
   112.0398 (74%), produced by the controlled aerobic fermentation of an aqueous nutrient medium by *Streptoverticillium hiroshimense*, ATCC 39070 at a temperature of 26° to 30° C. for at least 70 hours at pH 6.0 to 8.0.

2. A dopamine β-hydroxylase inhibitor of structural formula II:

H₃C—[pyridine ring with (OH)₃ substituent]—N   II empirical formula $C_6H_7NO_3$, and physical chemical characteristics:
 a. colorless crystalline compound,
 b. acidic aqueous UV data: 276 nm   261 sh,
 c. basic aqueous UV data: 304 nm   228 sh,
 d. acidic NMR (D₂O) chemical shifts: 2.48 (s)   4.82 (s),
 e. basic NMR (D₂O) chemical shifts: 2.30 (s)   4.68 (s),
 f. mass spectral data:
   M+ 171.0525 (100%)
   153.0449 (54%)
   125.0589 (32%)
   112.0398 (74%), produced by the controlled aerobic fermentation of an aqueous nutrient medium by *Streptoverticillium hiroshimense*, ATCC 39070 at a temperature of 26° to 30° C. for a least 70 hours at pH 6.0 to 8.0.

3. A process for producing the dopamine β-hydroxylase inhibitors of claims 1 and 2 which comprises *Streptoverticillium hiroshimense*, ATCC 39070 under controlled aerobic conditions in an aqueous nutrient medium at 26° to 30° C. for 70 to 120 hours, followed by isolation of each of Compounds I and II from the culture broth.

4. The process of claim 3 wherein the Compounds I and II are isolated from the crude broth by:
 a. filtering the crude broth through a filter aid,
 b. adjusting the pH to about 9 with an aqueous base,
 c. passing the basic solution through a basic ion-exchange resin,
 d. adjusting the eluate pH to about 3 with an aqueous acid,
 e. passing the acidic solution through an acidic ion-exchange resin, eluting with an aqueous base,
 f. concentrating the solution,
 g. lyophilizing the concentrate,
 h. treating the lyophilized solids with first methanol then water to give two solutions,
 i. further chromatographing the aqueous solution with first a polyacrylamide gel permeation column and second a dextran gel permeation column to provide Compound II in the first fraction,
 j. cooling the second fraction from said dextran gel permeation column to 0 C. to induce crystallization of Compound I.

5. A pharmaceutical composition for treating hypertension, said composition comprising an effective dopamine β-hydroxylase inhibiting amount of the compound of claim 1 or 2 and a pharmaceutical carrier.

6. A method of treating hypertension in humans which comprises administering thereto an effective amount of the dopamine β-hydroxylase inhibiting compound of claim 1 or 2 in a pharmaceutical carrier.

* * * * *